United States Patent [19]

Creusen et al.

[11] Patent Number: 5,498,339
[45] Date of Patent: Mar. 12, 1996

[54] PROCESS AND DEVICE FOR THE SEPARATION OF AN UNSATURATED HYDROCARBON FROM A FLUID MIXTURE WITH OTHER HYDROCARBONS

[75] Inventors: Raimond J. M. Creusen, Amersfoort; Everardus C. A. Hendriks, Utrecht; Jan H. Hanemaaijer, Oosterbeek, all of Netherlands

[73] Assignees: DSM N.V.; Nederlandse Organisatie Voor Toegepast Natuurwetenschappelljk Onderzoek Tno, both of Netherlands

[21] Appl. No.: 276,673

[22] Filed: Jul. 15, 1994

[30] Foreign Application Priority Data

Jul. 15, 1993 [NL] Netherlands ............ 9301245

[51] Int. Cl.$^6$ ............ B01D 61/00; B01D 11/04
[52] U.S. Cl. ............ 210/644; 210/651; 210/749; 210/765; 210/774; 210/805; 95/50; 95/288
[58] Field of Search ............ 210/650, 651, 210/774, 805, 806, 644, 749, 765; 95/50, 288

[56] References Cited

U.S. PATENT DOCUMENTS

| | | | |
|---|---|---|---|
| 3,758,605 | 9/1973 | Hughes et al. | 95/44 |
| 3,800,506 | 4/1974 | Hughes et al. | 585/818 |
| 4,060,566 | 11/1977 | Yahnke | 585/818 |
| 4,147,754 | 4/1979 | Ward, III | 423/224 |

FOREIGN PATENT DOCUMENTS

| | | |
|---|---|---|
| 362763 | 1/1977 | Austria . |
| 27613 | 8/1977 | Austria . |
| 857720 | 2/1978 | Belgium . |
| 0430331 | 6/1991 | European Pat. Off. . |
| 2400384 | 4/1977 | France . |
| 2737085 | 3/1979 | Germany . |
| 3181310 | 7/1991 | Japan . |
| 7708814 | 8/1977 | Netherlands . |
| 8902897 | 11/1989 | Netherlands . |
| 1577547 | 10/1980 | United Kingdom . |

*Primary Examiner*—Robert A. Dawson
*Assistant Examiner*—Kenneth M. Jones
*Attorney, Agent, or Firm*—Cushman Darby & Cushman

[57] ABSTRACT

A fluid mixture from which an unsaturated hydrocarbon has to be separated, is passed in the first stage at superatmospheric pressure to one side of a first semiselective gas separation membrane with a non-porous active layer, and a liquid complexing agent is passed along the other side of said first membrane, where said unsaturated hydrocarbon is bound through complexation in the interface of membrane and complexing agent. In the second stage said unsaturated hydrocarbon is dissociated from the complexing agent through temperature increase, the mixture of complexing agent and dissociated unsaturated preferably is passed at superatmospheric pressure to one side of a second semiselective membrane with a non-porous active layer and the unsaturated hydrocarbon migrates to the other side of the membrane and is discharged. Finally, the complexing agent is recycled.

7 Claims, 1 Drawing Sheet

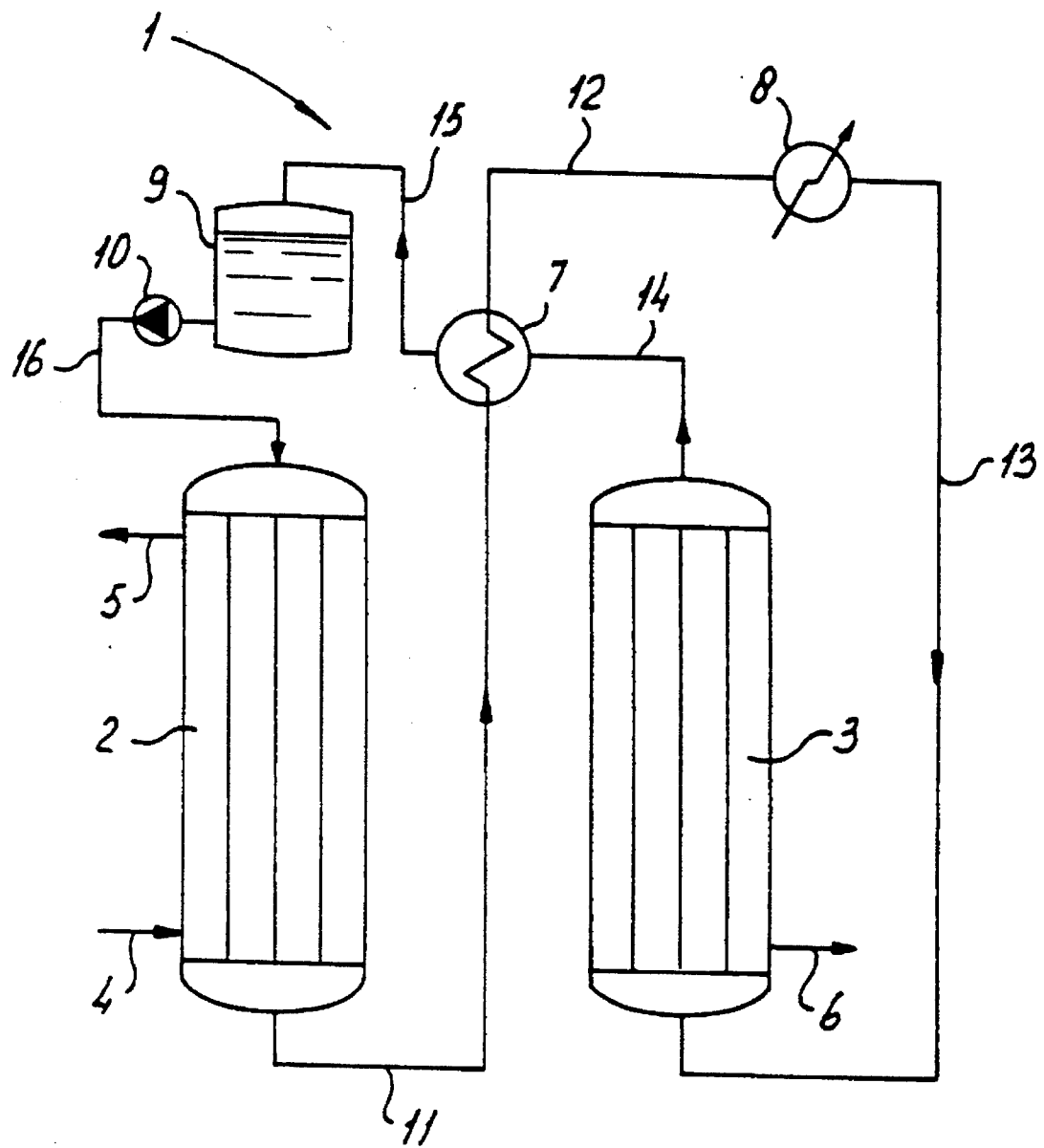

PROCESS AND DEVICE FOR THE SEPARATION OF AN UNSATURATED HYDROCARBON FROM A FLUID MIXTURE WITH OTHER HYDROCARBONS

The present invention relates to a process for the separation of an unsaturated hydrocarbon from a fluid mixture with other hydrocarbons wherein in a first stage the unsaturated hydrocarbon migrates through a membrane to a carrier fluid and in a second stage the unsaturated hydrocarbon is separated from the carrier fluid and removed.

Such a process is known from U.S. Pat. No. 5,057,641.

Unsaturated hydrocarbons such as ethene, propene, butene and styrene constitute a very important link in chemical production processes (polymers and other applications). They mostly occur in mixtures with other hydrocarbons, from which they often have to be separated. Usually cryogenic conditions are applied for the separation of ethene/ethane, propene/propane, butene/butane, styrene/ethylbenzene, etc. These separation processes are costly, however, both in terms of capital expenditure and operational costs. This is bound up with the fact that there is little distance between the boiling points of these hydrocarbons. In fact this is also the case with other chemical substances, for instance in the separation of nitrogen and oxygen.

Since the thirties already it has been known that unsaturated hydrocarbons have the property of complexing reversibly with metals and metal ions, in particular with transition metal ions such as $Ag^+$ and $Cu^+$. This has given rise to some separation processes based on extraction.

A well-known technique for application of reversibly complexing substances in a separation process is to immobilize them in the pores of a microporous membrane. Such a membrane is called an immobilized liquid membrane or facilitated transport membrane. Facilitated transport membranes for the separation of unsaturated and saturated hydrocarbons have received very much attention since the seventies, initially from Standard Oil Company (U.S. Pat. No. 3,758,603, U.S. Pat. No. 3,758,605 and U.S. Pat. No. 4,235,983) and Monsanto Company (U.S. Pat. No. 3,773,844). Recently as well other research groups have focused on this type of membrane (U.S. Pat. No. 5,015,268, GB-A-2,169,300, DE-A-3,924,102). This separation method is based on the use of microporous membranes, with silver salts (mostly nitrate, sometimes tetrafluoroborate) applied in the pores in an aqueous solution, sometimes supplemented with a thickening agent to inhibit leakage. The separation is effected under atmospheric conditions at both sides of the membrane, as a pressure drop would entail loss of complexing liquid. A flow of sweep gas (often nitrogen) is passed at the back of the membrane in order to pick up the unsaturated hydrocarbon, which is preferably permeating. In the circumstances of industrial practice the process conditions are undesirable; thus, ethene/ethane mixtures are often under a pressure of about 2 MPa, while reducing this pressure to 0.1 MPa would entail high compression costs afterwards. Moreover, the ethene has to be separated again from the sweep gas. Further, the membranes appeared to have a short life as the permeating ethene is saturated with water vapour leading to a drying out of the membrane.

As an alternative to facilitated transport membranes the application of microporous membranes has in general been proposed, with the complexing or extracting liquid contained between two membranes (U.S. Pat. No. 4,750,918). In this case as well the process is only carried out under atmospheric conditions and with application of a sweep gas as otherwise loss of complexing liquid would occur. Reference can also be given to WO 93-10889 and the article from Teramoto at al. in Journal of Membrane Science 45 (1989) pages 115–136 as well as in the proceedings of the 1987 International congress on membranes and membrane processes (held in Tokyo), where Teramoto also presented a spiral-type flowing liquid membrane module (page 812).

In order to make this type of separation processes suitable for commercial and economic application it is required that they can be carried out at elevated pressure (0.2–5 MPa), the permeate has to be discharged preferably without sweep gas, preferably at elevated pressure, the membrane has to be stable and should not lose its activity through loss of complexing agent and/or solvent, the process should generate sufficient flux and exhibit selectivity, and the product should be minimally contaminated with solvent.

U.S. Pat. No. 5,057,641 and U.S. Pat. No. 5,131,928 describe processes in which facilitated transport membranes are used and in which elevated pressures are applied, the permeate can be discharged without sweep gas and the membrane does not lose its activity. Due to the use of hydrophilic membranes and pores of a size of 10 to 200 Å, the capillary forces retaining the aqueous silver salt solution in the pores appear to be so great that at pressures of up to approx. 2.1 MPa the liquid is not expelled. Thus the process can handle liquid flows under pressure and the permeate flow can be discharged at reduced pressure and without sweep gas. Desiccation of the membrane is prevented by moistening the feed flow and by alternately or continuously passing at the permeate side the same complex solution as present in the pores. The flow permeating through the membrane is thus also present in said solution, from which it is separated in a flash drum at strongly reduced pressure.

These recent known methods have the drawbacks that the transport is slow, due to the sluggish diffusion of the resulting complex in the membrane (application of very narrow pores required in view of stability makes this diffusion additionally sluggish) and that very high compression costs are involved. As the permeating gas is discharged from the flash drum at reduced pressure and the pressure of this flow has to be restored, these separation processes are costly, while the gas discharged from the flash drum is saturated with water vapour, which entails an additional costly separation step. These known processes do not meet the requirements that it should be possible to discharge the product at elevated pressure, that there should be sufficient flux and selectivity and that the product should be minimally contaminated with water.

The object of the invention is to provide a process as indicated in the preamble hereof, whereby these requirements are fulfilled.

According to the invention this process is characterized in that in the first stage the fluid mixture is passed at superatmospheric pressure to one side of a first semiselective gas separation membrane with a non-porous active layer, and a liquid complexing agent is passed along the other side of said first membrane, where said unsaturated hydrocarbon is bound through complexation in the interface of membrane and complexing agent, in that in the second stage said unsaturated hydrocarbon is dissociated from the complexing agent through temperature increase, in that the mixture of complexing agent and dissociated unsaturated hydrocarbon is separated and in that the complexing agent is recycled. Preferably the mixture of complexing agent and dissociated, unsaturated hydrocarbon is passed at superatmospheric pressure to one side of a second semiselective membrane with a non-porous active layer wherein the unsaturated hydrocarbon migrates to the other side of the membrane and is discharged. The advantage of the instant invention is that the process of absorption (the complexation reaction) is separate and independantly adjustable from the process of desorption (the dissociation reaction); by using the temperature increase, a substantial dissociation can be obtained.

The complexation reaction thus takes place behind the first semiselective membrane with a non-porous active layer in the interface of membrane and permeate flow. A suitable membrane is any gas separation membrane having a non-porous active layer and being sufficiently permeable to the unsaturated hydrocarbon. The non-porous layer consists of a polymer film (optionally applied onto a porous carrier) in which the distances between the polymer chain segments usually vary from 2 and 20 Å. 'Active' relates to the layer that determines the membrane activity. This active layer preferably is at the side of the complexing agent. These membranes are very pressure resistant (in some cases to pressures higher than 10 MPa). Further, polymer films of elastomers have a very high permeability to a large number of hydrocarbons (higher by an order of 1 to 4 than the known facilitated transport membranes). The membranes are commercially available for a wide range of applications and consequently are relatively cheap. If properly chosen and/or modified they are selective towards water vapour. A further feature of these membranes is that they exhibit only very low or no selectivity towards for instance alkenes relative to alkanes and therefore they are only used to keep the complexing agent (for instance silver salt) and the solvent (water) separated from the feed flow at elevated pressure. Next to that, such membranes are also used to separate the permeate from the carrier fluid.

The fluid mixture may contain saturated and unsaturated hydrocarbons. The process of this invention can be used to separate paraffins from monoolefins, diolefins or acetylenes; diolefins from monoolefins; or acetylenes from paraffins, monoolefins or diolefins; as well as to separate a given aliphatically-unsaturated hydrocarbon from another of such materials in the same class where the members have differing complexing rates with the complexing agent. The feed need only contain a small amount of unsaturated hydrocarbon, as long as the amount is sufficient so that the unsaturated material to be separated selectively reacts with the metal complex to a significant extent, and thus at least one other component of the feed is less reactive or non-reactive with the complex-forming metal. The aliphatically-unsaturated materials of most interest with regard to separation by the method of the present invention have two to about twelve carbon atoms, preferably two to eight carbon atoms. The separation of aliphatically-unsaturated hydrocarbons from admixtures containing other hydrocarbons, such as the separation of ethene from ethane and methane, is of particular importance. Frequently such feed mixtures for the process contain about 1 to 50 weight percent ethene, about 0 to 50 weight percent ethane and about 0 to 50 weight percent methane. Propene is also an olefin in high demand, and its separation may be accomplished in accordance with the present invention. Another process that may be of special significance is the separation from ethene of minor amounts of acetylene. The process of the invention can also be used for the separation of aromatics from paraffins or cycloparaffins.

In the present invention those metals which can serve in the form of metal-containing cations to separate unsaturated hydrocarbons in the feed mixture through the formation of metal complexes of desired properties include, for instance, the transition metals of the Periodic Table of Elements having atomic numbers above 20. Included in these metals are those of the first transition series having atomic numbers from 21 to 29, such as chromium, copper, especially the cuprous ion, manganese and the iron group metals, e.g. nickel and iron. Others of the useful complex-forming metals are in the second and third transition series i.e. having atomic numbers from 39 to 47 or 57 to 79. Noble metals may be employed such as silver, gold and the platinum group, among which are platinum, palladium, rhodium, ruthenium and osmium. The useful base metals of the second and third transition series include, for example, molybdenum, tungsten, rhenium and the like. Various combinations of these complexing-forming metals may also be employed in this invention, either in the presence or absence of other non-metal or non-complexing metal cations. The concentration of the complexing agent is generally above 0.1 molar, preferably between 0.5 and 15 molar. Care should be taken that the concentration is always below the saturation point of the solution. The complexing agent preferably consists of a salt of silver or copper.

The membranes generally consist of a support structure and the active layer. For the support layer the following materials may be used: polysulfones, polyethersulfones, polyimides, polyacrylonitriles, polyphosphazenes, PVC (polyvinyl chlorides), PE (polyethylenes), PP (polypropylenes), PS (polystyrenes), nylons (normally glassy polymers are used). The active layer either consists of an elastomeric polymer or a glassy polymer. The following materials can be used:

Elastomeric materials:
silicones, e.g. polydimethylsiloxane (PDMS)
other Si-containing elastomers e.g.
polytrimethylsilylpropyne (PTMSP),
polyvinyltrimethylsilane (PVTMS)
polyurethanes/polyetherurethanes
natural rubber
ethene-propene (diene) rubbers (EP(D)M)
nitrile butadiene rubbers (NBR)
(All: with/without cross-linking).

Glassy polymers: all polymers with high gas permeability. Examples: polycarbonate; cellulose acetates; polyetherimide; polyphenylene oxide; polyoxydiazole; polystyrene; polyimides. These types of membranes generally have an overall thickness of between 10μ–10 mm, whereas the active layer has a thickness of between 0,01–10μ. The active layer of the membranes is preferably made of an elastomeric material, such as PDMS (polydimethyl siloxane) or EPDM (ethene propene diene rubber). Preferably, hollow fibre membranes are used.

The temperature at which the absorption (the complexation) is to be performed is above the melt temperature of the complexing liquid and generally between −10° and 50° C. The temperature at which the desorption (the dissociation) is performed is increased in respect to the absorption temperature, preferably with at least 5° C. The desorption temperature generally is between 10° and 150° C.

The pressure at which the process of the present invention can be performed is not critical and can be the same for absorption and desorption; a pressure reduction from absorption to desorption is also possible. The pressures are generally between 0.05 and 5 MPa, preferably between 0.2 and 2 MPa. In the second stage use may be made of a sweep fluid, but preferably the unsaturated hydrocarbon is obtained from the second stage without using such a sweep fluid.

To avoid potential reduction of the complexing agent during the process, the carrier fluid may contain or be supplemented with an oxidator, like nitric acid or hydrogen peroxide. Also other additives, e.g. to lower the water activity, can be used.

The invention also relates to a device with which the process described above can be carried out. This device comprises a first system of semiselective gas separation membranes comprising a non-porous active layer, means with which a fluid mixture is supplied at superatmospheric pressure to one side of the membranes, means with which a liquid complexing agent is supplied to the other side of the membranes, means with which to heat the complexing agent with bound unsaturated hydrocarbon which has flowed along the other side of the membrane and means to separate the unsaturated hydrocarbon from the complexing agent and to recycle the complexing agent. Preferably the device further comprises a second system of semiselective gas separation membranes comprising a non-porous active layer, means with which at superatmospheric pressure the heated complexing agent and the unsaturated hydrocarbon dissociated from it are passed along one side of the membranes of the second system, means with which to remove the unsaturated hydrocarbon that has migrated through said membranes of the second system.

The invention will now be elucidated with reference to the schematic FIGURE.

The FIGURE shows an example of a device 1 with which the process according to the invention is carried out. The device comprises a first separation unit 2 where the unsaturated hydrocarbon is absorbed into a carrier fluid, and a second separation unit 3 where the unsaturated hydrocarbon is removed from the carrier fluid. The separation units are incorporated in a circuit 11–16 through which the carrier fluid is circulated by means of a pump 10. Heating elements 7,8 are integrated in the first part 11, 12, 13 extending from the first separation unit to the second one. At 8 the carrier fluid is heated by means of a heating device, then it is passed through the second separation unit, whereupon the carrier fluid is passed to heat exchanger 7 via line 14 and flows on to buffer 9 via line 15. By means of heat exchanger 7 the heat of the carrier fluid coming from the second separation unit is used to preheat the carrier fluid coming from the first separation unit, whereby the fluid coming from the second separation unit is cooled. In the buffer 9 the carrier fluid freed of the unsaturated hydrocarbon is collected, after which it is circulated through the circuit 11–16 again via pump 10 and line 16.

The first separation unit further comprises feed lines 4 for the supply of a fluid mixture to be separated and means of discharge 5 for removal of a fluid mixture that has been depleted with the unsaturated hydrocarbon to be separated. The second separation unit 3 has means of discharge 6 for removal of the separated unsaturated hydrocarbon.

The first and the second separation unit (2 resp. 3) are provided with membranes. In particular for unit 2 a system of hollow fibre membranes (high exchange areas) is preferred. The carrier fluid, comprising an aqueous solution with complexing substance such as silver and/or copper ions, is passed through the lumens of the hollow fibres. The fibers are equipped with the active layer at the lumenside of the fibers.

Via feed channels 4 a mixture of alkanes and alkenes is supplied to the first separation unit 2. The alkanes and alkenes can both move freely through the first membrane to the carrier fluid. Both the alkanes and alkenes are fractionally dissolved in the carrier fluid, while the alkenes form a complex compound with the silver and/or copper ions. In this way the fluid mixture supplied via feed lines 4 is substantially freed of alkenes. Next the fluid mixture, in which the alkenes are bound in complexes with the silver and/or copper ions, is preheated in heat exchanger 7, supplied to heating element 8 via line 12, where the carrier fluid is heated further. As a consequence of the temperature increase the alkenes are dissociated from the copper and/or silver ions, so that, when the carrier fluid has been supplied to the second separation unit 3 via line 13, they can escape out of the carrier fluid by gaspermeation and/or pervaporation via the second membrane, after which the product that is released, which substantially contains alkenes, is removed via the means of discharge 6.

The invention will be elucidated further by means of the following examples. In all examples, use was made of membranes consisting of a polyethersulfone as support layer (thickness about 50μ) and an active layer of PDMS (thickness 3μ). The surface areas for absorption side and desorption side were 300 cm².

Example I
Process: ethane/ethene separation
Feed: 17 nl/h, 88% ethene, 12% ethane (v/v)
Gas pressure: 0.3 MPa (absorption side) 0.1 MPa (desorption side)
Pressure of carrier fluid: 0.4 MPa
Temperature: 22° C. (absorption side) 30° C. (desorption side)
Complexing agent: 6M $AgNO_3$, in water; 23 l/h
Reject: 3.8 nl/h, 50% ethene, 50% ethane (v/v)
Product: 13.2 nl/h, 99.1% ethene, 0.9% ethane (v/v).

Example II
Process: methane/ethene separation
Feed: 17 nl/h, 88% ethene, 12% methane (v/v)
Gas pressure: 0.45 MPa (absorption side) 0.1 MPa (desorption side)
Pressure of carrier fluid: 0.4 MPa
Temperature: 23° C. (absorption side) 28° C. (desorption side)
Complexing agent: 4M $AgNO_3$, in water ; 23 l/h
Reject: 3.2 nl/h, 42.5% ethene, 57.5% methane (v/v),
Product: 13.8 nl/h, 98.7% ethene, 1.3% methane (v/v).

Example III
Process: ethane/ethene separation
Feed: 17 nl/h, 88% ethene, 12% ethane (v/v)
Gas pressure: 0.27 MPa (absorption side) 0.1 MPa (desorption side)
Pressure of carrier fluid: 0.34 MPa
Temperature: 15.3° C. (absorption side) 25.1° C. (desorption side)
Complexing agent: 6M $AgNO_3$, in water; 23 l/h
Reject: 6.2 nl/h, 68% ethene, 32% ethane (v/v)
Product: 10.8 nl/h, 99.4% ethene, 0.6% ethane (v/v).

Example IV
Process: methane/ethene separation
Feed: 15 nl/h, 88% ethene, 12% methane (v/v)
Gas pressure: 0.45 MPa (absorption side) 0.15 MPa (desorption side)
Pressure of carrier fluid: 0.4 MPa
Temperature: 23° C. (absorption side) 28° C. (desorption side)
Complexing agent: 4M $AgNO_3$, in water; 23 l/h
Reject: 4.0 nl/h, 55% ethene, 45% methane (v/v),
Product: 11.0 nl/h, 98.7% ethene, 1.3% methane (v/v).

Example V
Process: ethane/ethene separation
Feed: 17 nl/h, 88% ethene, 12% ethane (v/v)
Gas pressure: 0.46 MPa (absorption side) 0.25 MPa (desorption side)
Pressure of carrier fluid: 0.60 MPa
Temperature: 21.7° C. (absorption side) 30.1° C. (desorption side)

Complexing agent: 6M AgNO$_3$, in water; 69 l/h
Reject: 2.9 nl/h, 35% ethene, 65% methane (v/v),
Product: 14.1 nl/h, 98.9% ethene, 1.1% methane (v/v).

We claim:

1. A process for the separation of at least one specific unsaturated hydrocarbon from a fluid mixture with other hydrocarbons which comprises:

a first stage comprising (i) passing the fluid mixture containing said unsaturated hydrocarbon at superatmospheric pressure to one side of a first semiselective gas separation membrane with a non-porous active layer which is permeable to unsaturated hydrocarbons, and (ii) passing a stream comprising a liquid complexing agent on the other side of said first semiselective gas separation membrane, whereby the unsaturated hydrocarbon migrates through said first semiselective gas separation membrane with said non-porous active layer to the liquid, wherein said at least one specific unsaturated hydrocarbon is bound through complexation in the interface of the membrane and said liquid complexing agent; and a second stage which comprises (i) separating and removing the unsaturated hydrocarbon from the complexing agent, wherein in the second stage said unsaturated hydrocarbon is dissociated from the complexing agent by increasing the temperature, and (ii) the complexing agent is recycled.

2. A process according to claim 1, wherein the mixture of complexing agent and dissociated unsaturated hydrocarbon is passed at superatmospheric pressure to one side of a second semiselective membrane with a non-porous, but permeable active layer and in that the unsaturated hydrocarbon migrates to the other side of the membrane and is discharged.

3. A process according to claim 1, wherein the complexing agent comprises a salt of silver or copper.

4. A process according to claim 1, wherein the membranes used in the first stage are hollow fibre membranes.

5. A process according to claim 1, wherein the active layer of the membranes is made of an elastomeric material, such as PDMS or EPDM.

6. A device for separating at least one specific unsaturated hydrocarbon from a fluid mixture containing other hydrocarbons which comprises:

a first system of semiselective gas separation membranes comprising a non-porous but permeable active layer, means for supplying a fluid mixture at super-atmospheric pressure to one side of the membranes, means for supplying a stream comprising a liquid complexing agent to the other side of the membranes, means for heating the complexing agent with bound unsaturated hydrocarbon which has flowed along the other side of the membrane, means for separating the at least one specific unsaturated hydrocarbon from the complexing agent and means for recycling the complexing agent.

7. A device according to claim 6, further comprising a second system of semiselective gas separation membranes comprising a non-porous active layer, means for passing at superatmospheric pressure, the heated complexing agent and the component dissociated from it along one side of the membranes of the second system, and means for removing the component that has migrated through said membranes of the second system.

* * * * *

UNITED STATES PATENT AND TRADEMARK OFFICE
CERTIFICATE OF CORRECTION

PATENT NO. : 5,498,339
DATED : March 12, 1996
INVENTOR(S) : CREUSEN et al.

It is certified that error appears in the above-indentified patent and that said Letters Patent is hereby corrected as shown below:

On the title page Item 73, change "Natuurwetenschappelljk Onderzoek Tno" to read --Natuurwetenschappelijk Onderzoek TNO--.

Signed and Sealed this

Twenty-ninth Day of April, 1997

Attest:

BRUCE LEHMAN

Attesting Officer

Commissioner of Patents and Trademarks